United States Patent [19]
Weigl

[11] Patent Number: 5,919,043
[45] Date of Patent: Jul. 6, 1999

[54] TWO-PART DENTAL IMPLANT WITH METAL LAYER GALVANIZED THEREON

[75] Inventor: Paul Weigl, Bad Homburg, Germany

[73] Assignee: C. Hafner GmbH & Co., Pforzheim, Germany

[21] Appl. No.: 08/969,501

[22] Filed: Nov. 13, 1997

[30] Foreign Application Priority Data

Nov. 16, 1996 [DE] Germany .................... 196 47 489

[51] Int. Cl.⁶ .................................................. A61C 8/00
[52] U.S. Cl. ............................................. 433/172; 433/173
[58] Field of Search .................................. 433/172, 173, 433/174, 175, 176

[56] References Cited

U.S. PATENT DOCUMENTS

| | | | |
|---|---|---|---|
| 5,328,371 | 7/1994 | Hund et al. ........................... | 433/173 |
| 5,447,434 | 9/1995 | Shaw .................................... | 433/173 |
| 5,607,304 | 3/1997 | Bailey et al. ......................... | 433/174 |
| 5,785,524 | 7/1998 | Wolf .................................... | 433/173 |

Primary Examiner—John J. Wilson
Attorney, Agent, or Firm—Klaus J. Bach

[57] ABSTRACT

In a two-part dental implant including an implant body and an implant abutment mounted onto the implant body, a metal layer is galvanically deposited on the contact area of the implant body or the abutment and the two are firmly engaged by a mounting screw generating a contact force which is sufficient to cause plastic deformation of the galvanically deposited metal layer which, in this way, fills any gaps between the implant body and the abutment.

5 Claims, 1 Drawing Sheet

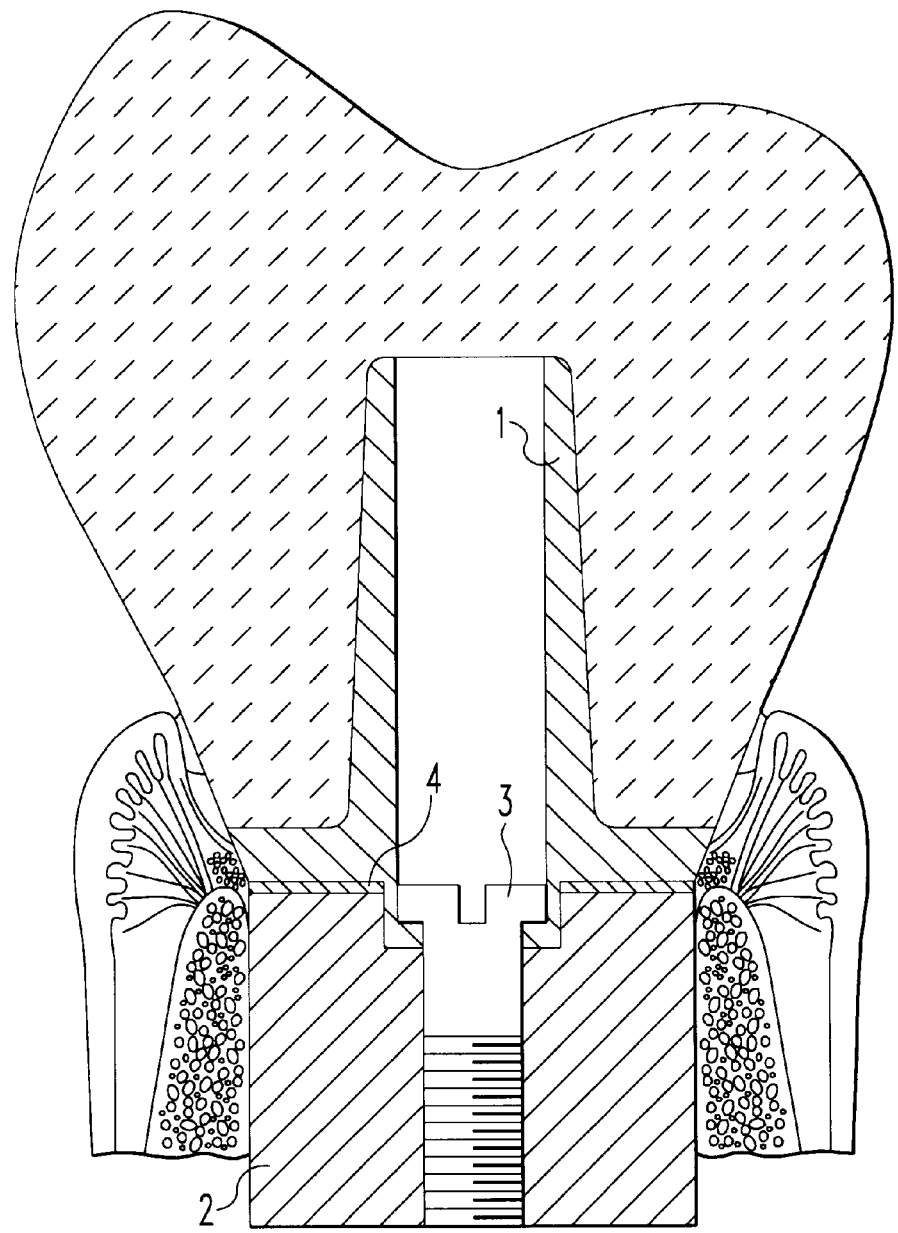

TWO-PART DENTAL IMPLANT WITH METAL LAYER GALVANIZED THEREON

BACKGROUND OF THE INVENTION

The invention resides in a two-part dental implant with an implant abutment and an implant body.

In dental medicine, the loss of a tooth is more and more often compensated for by dental implants. Also, for the replacement of other body parts, such as ears, eyes, or fingers, artificial parts can be adequately anchored in an elegant manner by modified dental implant systems.

The implant is inserted into a bone bearing structure, which is generated by surgical measures. If the implant is subjected during the healing phase to no loads or only to small loads, it is very likely that an onkylotic jointure between the implant body and the adjacent bone structure is formed. For a complete osseointegration, a lower jaw implant requires about three months and an implant in the upper jaw or in other areas requires about five to six months.

In order to provide for this time interval a clinically load-free situation for the inserted implant, the implant consists preferably of two parts.

A dental implant can be divided into three areas: the enossal implant body, the region of penetration through the soft tissue and the intra-oral part for receiving the superstructure. Today, mostly rotation-symmetrical enossal implant bodies are used. The intra oral part of the implant has the greatest variability as far as shape and functions are concerned. Depending on the planned use of the implant post, the abutment may be shaped like a tooth prepared to receive a crown or like a support element on a vital tooth (head anchor, web, magnet attachment). For epithesis, mainly magnet attachments and bottom anchors are used.

With a two-step implantation procedure, the implant is adopted in a sub- or transepithelial manner. Only after the healing period is the post for the reception of the prosthesis, the so-called implant abutment, screwed onto the enossal implant body. The division of the implant into an enossal body and an implant abutment to be screwed onto the enossal body requires a two- or multiple part implant system. The connections between these two- or multiple part implant systems are of different designs, depending on the manufacturer. In all systems, however, there are inaccuracies between the joining surfaces of the enossal implant body and the implant abutment—which are caused by manufacturing tolerances—inspite of the relatively high torques applied to the connecting screws at the interface between the enossal implant bodies and the abutment.

The jointure gap is often found in the peri-implantal connective tissue sleeve. The peri-implantal soft tissue is, in contrast to the periodontal tissue, a scar tissue with bad blood circulation, which is formed on the highly polished surface of the implant or the super-construction. It generally reacts with respect to insufficient mouth hygiene, rough surfaces and projecting crown edges in a more sensitive way than the dento-gingival unit of the natural tooth. The causes and particularly ways of containing inflammations of this tissue—the so-called peri-implantal mucosities—are presently the subject of research. The peri-implantitis causes—analog to paradontitis—tissue resorptions, which lead to crater-like bone collapse around the implant and expose the enossal implant body to plaque deposits. This results in a progressive cirulus vitiosus, which rapidly leads to a loss of the implant.

In a gap between the enossal implant body and the abutment of a two part implant system, ideal growth conditions are generated for anaerobic pathogens. It is likely that these gaps have a negative influence on the state of the soft tissue sleeve and induce a peri-implantal mucositis or peri-implantitis. In animal experiments made recently infiltration in the area of the connection was histologically determined, inspite of strict plaque control and clinically inflammation-free soft tissue.

Even with a precise extra-oral fitting of the abutment, no bacteria-tight jointures can be achieved as the newest research results show.

In addition, substantial problems occur with two-part implant system when the abutment loosens, which happens quite frequently. The extremely high number of load changes on the implant during chewing and swallowing causes the connecting screw to come lose. Particularly with firmly cemented restorations, the prosthesis superstructure must be made and installed new after it has become lose which is costly and time consuming.

There are no types of implants available which hold the screw safely in place. Even the use of a screw with a relatively large conical screw head, which is screwed into a form-fitting female structure in the enossal implant body, has not been found, in clinical use, to eliminate the problem or even significantly reduce the chance of the abutment to become lose. The efforts of the implant manufacturers to optimize the tightness of their two-part implant systems usually culminate in the provision of a silicon ring in the gap between the two parts. Such silicon rings however have insufficient resistance to the environment to which they are exposed in the mouth, which leads to substantial servicing requirements for the implant patient. Because of these important clinical disadvantages of silicon, the clinical use is really very questionable inspite of the fact that it has been shown that a better seal can be provided with the use of silicon rings.

It is the object of the invention to provide a two-part implant without the problems by which present implants are afflicted. The implant abutment should have a germ-tight connection to the enossal implant body and a loosening of the mounting screw during the life of the implant should not be possible.

SUMMARY OF THE INVENTION

In a two-part dental implant including an implant body and an implant abutment mounted onto the implant body, a metal layer is galvanically deposited on the contact area of the implant body or the abutment and the two are firmly engaged by a mounting screw generating a contact force which is sufficient to cause plastic deformation of the galvanically deposited metal layer which, in this way, fills any gaps between the implant body and the abutment.

It is particularly advantageous to use as the plastically deformable metal layer a bio-compatible metal layer like gold or respectively a layer of fine gold. The metal layer is plastically deformed by the screw-generated pressure. The abutment according to the invention is characterized by a gold layer, which is formed by direct galvanic deposition onto the contact areas with the enossal implant body. The layer of fine gold may be deposited on the full contact surface or only on the peripheral edge area of the implant, that is, in the contact area with the peri-implantate soft tissue. The thickness of the gold layer is, depending on the implant design and the average manufacturing accuracy, about 10 $\mu$m greater than the mounting gap normally occurring between the enossal implant body and its abutment. Such over-dimensioning is done in order to be able to utilize the plastic properties of galvano-formed fine gold structures. Since the implant material has a much greater modulus of elasticity and a greater yield strength than a galvanically formed layer of fine gold, the gold layer is deformed by the pressure generated during tightening of the mounting screw between the implant abutment and the enossal implant body. The gold layer fills the gaps caused by manufacturing tolerances in a germ-sealing manner provided the gaps are not essentially larger than the layer thickness of the fine gold.

The plastic deformation of the fine gold layer furthermore provides for pre-tensioning of the screw and for a fully symmetrical force transmission by way of the fully form-fitting contact areas between the implant abutment and the enossal implant body. Both contribute to preventing the mounting screw from becoming lose during the life period for which the implant is designed even with frequent load changes.

Other metallic materials are suitable for galvanic deposition only if they have a high bio-compatibility, as it is the case for example for platinum, and if they are not subject to corrosion in connection with the implant material.

Specific features and advantages of the invention will become apparent from the following description of a particular embodiment with reference to the accompanying drawings.

BRIEF DESCRIPTION OF THE DRAWINGS

The sole FIGURE shows a schematically particular embodiment of a jaw implant.

DESCRIPTION OF A PREFERRED EMBODIMENT

The FIGURE shows in an axial cross-sectional view an abutment 1, which is mounted on an implant body 2 by means of a screw 3. A mounting gap between the abutment 1 and the implant body 2 is totally filled with a fine gold layer 4, which is disposed on the abutment 1. As a result, the peri-implantal soft tissue 5 is not subjected to chronic irritations generated by a microbe infestation of a jointure gap between the abutment 1 and the implant body 2. In addition, the screw 3 remains tensioned whereby, together with the form fitting mounting and the uniform force transmission by way of the deformable fine gold layer 4 between the abutment 1 and the implant body 2, the screw is firmly held in position.

It may be possible to use the invention also in the crano-facial area for the reception of eyes, noses and ear epitheses.

What is claimed is:

1. A two-part dental implant comprising an implant body and an implant abutment mounted onto said implant body so as to be in firm contact therewith over a contact area, one of said implant body and said implant abutment having, in said contact area, a metal layer galvanically deposited thereon, and mounting means for firmly engaging said implant abutment with said implant body with a force sufficient to cause, in said contact area, plastic deformation of said galvanically deposited metal layer.

2. An implant according to claim 1, wherein said metal layer consists of a bio-compatible material having fine gold-like properties.

3. An implant according to claim 1, wherein said metal layer consists of fine gold.

4. An implant according to claim 1, wherein said metal layer has a thickness of 5 to 20 µm.

5. An implant according to claim 1, wherein said metal layer has a thickness of 10 to 15 µm.

* * * * *